US006559351B1

(12) United States Patent
Eakin

(10) Patent No.: US 6,559,351 B1
(45) Date of Patent: May 6, 2003

(54) WOUND DRESSING

(75) Inventor: Thomas George Eakin, Newtownards (GB)

(73) Assignee: T.G. Eakin Limited, Comber County Down (GB)

( * ) Notice: Subject to any disclaimer, the term of this patent is extended or adjusted under 35 U.S.C. 154(b) by 0 days.

(21) Appl. No.: 09/517,707

(22) Filed: Mar. 2, 2000

Related U.S. Application Data

(63) Continuation of application No. PCT/GB98/02623, filed on Sep. 1, 1998.

(30) Foreign Application Priority Data

Sep. 5, 1997 (GB) ............................................. 9718923

(51) Int. Cl.$^7$ ................................................. A61F 13/00
(52) U.S. Cl. ............................ 602/56; 604/361; 602/41
(58) Field of Search ............................. 602/41, 52, 58, 602/56; 604/361

(56) References Cited

U.S. PATENT DOCUMENTS 4,341,207 A  *  7/1982  Steer et al.
4,538,603 A  *  9/1985  Pawelchak et al.

* cited by examiner

Primary Examiner—Nicholas D. Lucchesi
Assistant Examiner—Lalita Hamilton
(74) Attorney, Agent, or Firm—Wallenstein & Wagner, Ltd.

(57) ABSTRACT

A wound dressing is formed from a covering release layer, a dressing layer, an indicator layer, a transparent or translucent indicator bonding layer and a transparent or translucent outer covering. The indicator layer contains a dye which changes color on contact with water. When the dressing layer becomes saturated, water permeates the indicator layer and triggers a color change. The color change is visible through the indicator bonding layer and outer covering and shows a carer that the dressing needs to be replaced.

7 Claims, 1 Drawing Sheet

WOUND DRESSING

This application is a continuation of International Application No. PCT/GB98/02623, filed Sep. 1, 1998, now pending (which is hereby incorporated by reference).

TECHNICAL FIELD

The present invention relates to wound dressings and, in particular, to occlusion dressings. The wound dressing of the invention has a visible indicator so that a user can see when the dressing and determine whether it should be changed. The saturation colour change, depending on the amount of exudate, may in most cases indicate that a change of dressing is necessary.

BACKGROUND OF THE INVENTION

Wound dressings are widely used for many types of epithelial wounds and, in general, need to be changed at regular intervals to ensure that the wound and surrounding area remains as clean as possible. Occlusion dressings function by sealing the wound, thus preventing external contamination and keeping the tissue moist, which promotes healing. It is undesirable to change the dressing frequently since this negates the effect of the occlusion principle. However, when the dressing is saturated, it can no longer perform its function effectively. It would therefore be useful if the patient and carers responsible for changing wound dressings could be alerted when a change of dressing is required.

Dressings which indicate when they are saturated are known and one example is the dressing sold by Convetec under the trade mark SignaDRESS. In the SignaDRESS™ dressing, fluid leaks from the wound into an area behind an impermeable outer covering of the dressing causing a blister to become visible. Once the edge of the blister reaches an indicator line marked on the outer surface of the dressing, changing is required. The SignaDRESS™ dressing does, however, have certain disadvantages, the main one being that it is covered by a polymer film which restricts the flexibility of the dressing and prevents it from conforming to the contours of the wound site. In addition, the indicator is merely a blister on the surface of the dressing and may, in some cases, be difficult to read and, if allowed to enlarge, may become a pouch of fluid excessive to the requirements of a healing environment.

The present invention also provides a dressing which indicates when it needs to be changed. However, it functions in a completely different way from the SignaDRESS™ dressing.

SUMMARY OF THE INVENTION

In the present invention, therefore, there is provided a wound dressing comprising:
a. a covering release layer;
b. a dressing layer;
c. an indicator layer;
d. a transparent or translucent covering;
characterised in that the indicator layer comprises a non toxic indicator substance, which changes colour on contact with water, mixed with a diluting agent and the bonding layer comprises a water-impermeable mobile sticky polymer capable of bonding the indicator layer to the dressing layer and to the outer covering.

The advantage of the dressing of the invention is that when it becomes saturated and needs to be changed, liquid penetrates into the indicator layer, causing the indicator substance to change colour. The colour change is visible through the indicator bonding layer and the outer covering and so it is obvious to the person responsible that the dressing needs to be changed. In addition, unlike the SignaDRESS™ dressing, the indicator in the dressing of the present invention covers the entire area of saturation of the dressing. This makes it easy to tell if the dressing needs to be changed.

Covering release layers for dressings are known and are designed to be loosely attached to the dressing layer and impermeable to microorganisms. Examples of known types of covering release layers include paper with a siliconised surface or paper coated with a polymer. For this invention, polymer coated papers are preferred as they do not tend to leave residues on the dressing, which can be a problem with siliconised covering release layers. Paper coated with polyethylene has been found to be a particularly suitable covering release layer for use in this invention.

The dressing of the invention may be of any known type, for example an antiseptic-impregnated gel or other type of fibrous medium such as gauze. However, it is very much preferred that the dressing is of the hydrocolloid type. Hydrocolloid dressings are well known in the art and consist of a fine particulate powder which gels in the presence of body fluids and/or water. The hydrocolloid dressing may consist of a powdered gelling substance suspended in a colloidal suspending agent.

Gelling substances which have been used in hydrocolloid dressings include starch and, more recently, sodium carboxymethylcellulose, pectin and other moisture-absorbing particulate substances. Mixtures of any of these gelling agents may also be used.

The suspending agent should be water impermeable and mobile and it should be chosen such that it does not create an adverse reaction when placed in contact with a wound. Examples of suitable suspending agents include polyisobutylene, which may be mixed with one or more other polymers, such as polyethylene, and some carbohydrates. In some types of hydrocolloid dressings, the gelling substance and suspending agent have been replaced by a hydrogel.

A particularly suitable hydrocolloid dressing for the present invention is formed from sodium carboxymethylcefiulose, alone or with starch or other moisture absorbing particles suspended in polyisobutylene, which may be mixed with polyethylene or other polymers. The exact composition of the hydrocolloid will be chosen to provide the desired degree of moisture retention. One skilled in the art of hydrocolloid dressings would be aware of how this could be achieved.

The hydrocolloid dressing slowly absorbs moisture, which is retained in the area of the wound. There is, in many cases, a relationship of proportionality between the thickness of the dressing and the time taken for it to become saturated. In addition, the permeability of the dressing may be affected if the dressing is sterilized by irradiation.

One of the features of hydrocolloid dressings, which makes them particularly suitable for use in the present invention, is that the proportions of gelling substance and suspending agent can be chosen so that the dressing is impermeable to moisture until it become saturated. This means that no moisture reaches the indicator substance until the dressing is saturated and needs to be changed.

In dressings consisting of hydroxymethylceUulose (and optionally starch) suspended in polyisobutylene or a mixture of polyisobutylene and polyethylene, a suitable ratio of gelling substance to suspending agent is about 1:1.

The indicator substance may be placed in small dots on the outer surface of the dressing layer. Alternatively, the indicator layer may comprise a thin layer of a powdered indicator substance, which may be mixed with a diluent. The diluent is used in order to emphasise the colour change of the indicator substance. Thus, suitable diluents are of a light colour, often white, which will partially conceal the original colour of the dry indicator substance and make the colour change more noticable when the indicator substance is wet. Diluents which may be used in the dressing of the invention include sodium carboxymethyl cellulose and magnesium carbonate.

Suitable indicator substances include soluble dyes such as 0.25% crystal green, Mercurochromet™, cobalt salt moisture indicator and gentian violet or, alternatively, it would be possible to use any indicator with a colour change activated by enzymic catalytic action, provided that the appropriate enzyme is also provided in the indicator layer. An example of a system which uses an enzyme-activated colour change is the system used in analysing urine for the presence of glucose. This system employs glucose oxidase, peroxidase and a colourless hydrogen donor and, on contact with glucose, a coloured compound is produced. If glucose, as well as the enzymes, were imobilised in the indicator layer, contact with moisture would allow the components of the system to mix so that the colour change is produced. There are many other enzyme-activated colour change systems and any of these could be used in a similar manner to the glucose oxidase/peroxidase system.

The covering layer should be impermeable to moisture in order to prevent exudate from leaking from the wound to the outside of the dressing. It should also be capable of bonding the indicator layer to the remainder of the dressing to prevent leakage of the indicator substance. Preferably, the covering layer will be extremely flexible so that the dressing will conform to the contours of the patient's skin in the area of the wound.

It is greatly preferred that the covering layer of the present invention should, in fact, be composed of two sub-layers, an indicator bonding layer and an outer covering. The particular advantage of this arrangement is that it provides virtually no trauma to the wound since the layers can be chosen to conform to the contours of the skin surface. In addition, the appearance of a dressing having a two-part covering layer has proved to be more acceptable. Both of the sub-layers should, of course, be transparent or translucent so that the colour change in the indicator layer is visible.

The function of the indicator bonding layer is, as its name suggests, to bond the indicator layer to the dressing layer and to the outer covering. It may be formed from a mobile sticky polymer and suitable polymers include those used as suspending agents in a hydrocolloid dressing. Thus, polyisobutylene has proved to be particularly suitable for use in the indicator bonding layer of the dressing. The indicator bonding layer may be applied as a coating on top of the indicator layer and this will usually be the case when polymers such as polyisobutylene are used. Alternatively, however, the indicator bonding layer may be applied as an evaporating solution of a polymer, which acts as a carrier for the indicator. In this case, care should be taken that the polymer is water permeable so that it does not seal in the indicator and prevent it from being contacted by moisture seeping through the dressing.

The thickness of the indicator bonding layer will largely depend on the material of which it consists. Typically, however, the indicator bonding layer will be very thin, preferably from about 0.1 mm to 1.0 mm in thickness. Usually the thickness of the indicator bonding layer will be from about 0.4 mm to 0.6 mm and most preferably about 0.5 mm.

The covering layer, or when used, the outer covering sub-layer, may have a larger area than the other layers of the dressing and, in the area surrounding these layers, it may be backed with an adhesive which will adhere to the skin surrounding a wound. In this case, the covering release paper will be of the same area of the outer covering so that it protects the adhesive.

Suitable outer coverings for occlusion dressings are known and, in general consist of thin films of a polymeric material or thin foam films.

However, although any known type of outer covering can be used, a particularly suitable material is a thin, porous, breathable film of low density polyethylene with small perforations spaced at intervals of, for example 0.25 mm. The film will typically be of from 1 to 20 $\mu$m in thickness. A suitable film is manufactured by Tredgar Films under the trade mark FLEXFILM and the use of a dressing with this type of film as an outer covering forms a further aspect of the present invention.

In a second aspect of the invention, there is provided a dressing comprising:

a. a covering release layer;

b. a dressing layer;

c. an outer covering;

characterised in that the outer covering is formed from a porous breathable film of low density polyethylene having a thickness of from 1 to 20 $\mu$m and perforations spaced at intervals of from 0.1 to 0.5 mm.

The advantage of using this type of film as the outer covering for the dressing of the present invention is that it has little elasticity but the perforations allow it to conform to any shape without folding or creasing. This means that the dressing can be placed on any part of the body without folding it and without putting causing traumatic stress, which frequently causes irritation in the area surrounding the wound and consequent discomfort to the patient. The flexibility of this outer covering also allows the patient some movement.

The conformity and lack of stress provided by a dressing with this type of outer covering is in contrast to the problems which accompany the use of conventional outer coverings. Thin polymer films may be stretchable but, in most cases, their elasticity creates trauma in the wound and surrounding area. Thin foam films are an improvement but still either limit the conformity of the dressing, create trauma or both.

Suitably the perforations in the film are spaced at intervals of 0.2 mm to 0.3 mm and typically 0.25 mm.

Preferred covering release layers and dressing layers are equivalent to those of the first aspect of the invention and it is preferred that the dressing also contains the indicator bonding layer of the first aspect of the invention.

BRIEF DESCRIPTION OF THE DRAWINGS

The invention will now be further described by way of example only with reference to the following drawing in which.

DETAILED DESCRIPTION OF THE PREFFERED EMBODIMENTS

Figure 1:
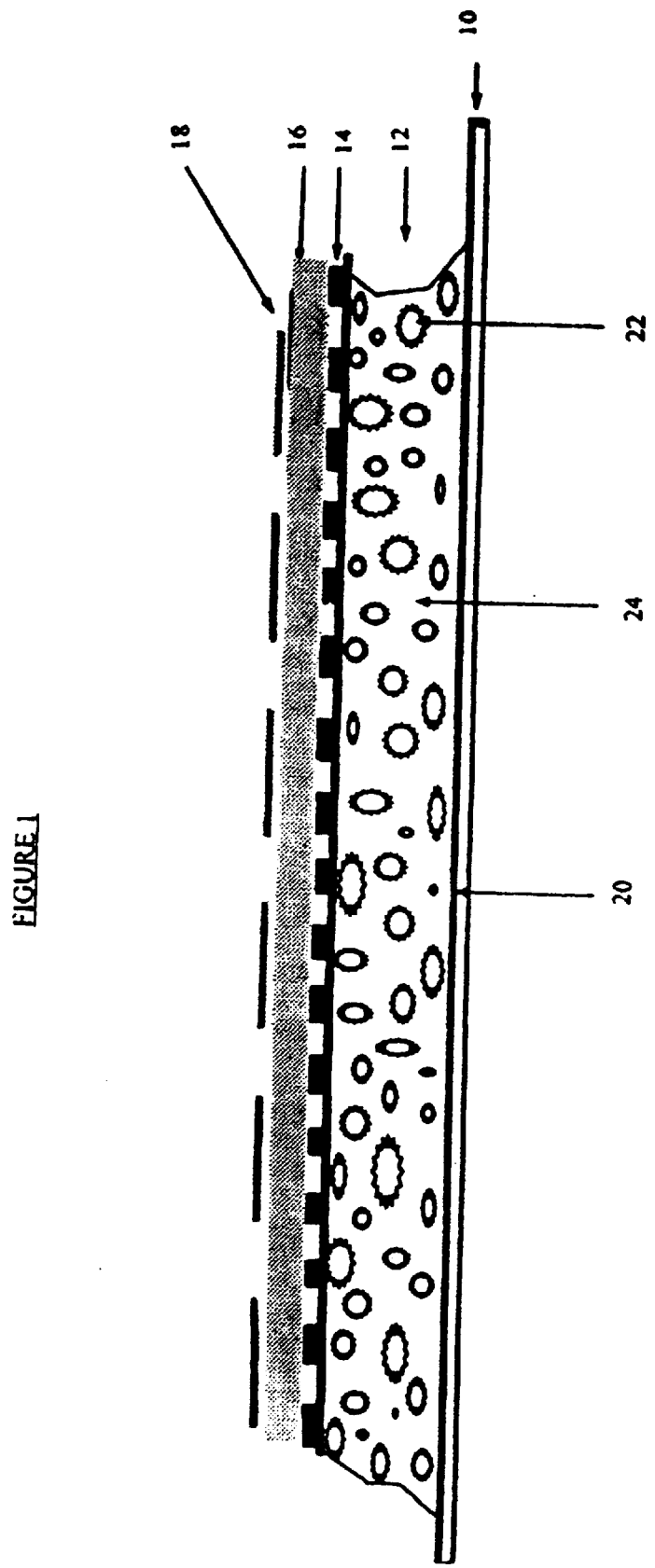
FIG. 1 is a cross section through a wound dressing of the present invention.

The dressing consists of a covering release layer (10), a dressing layer (12), an indicator layer (14), an indicator bonding layer (16) and an outer covering (18). The covering release layer (10) is formed from paper with polyethylene coat (20) on the surface adjacent the dressing layer (12). The polyethylene coat (12) ensures that the paper is easily detached from the dressing and is impermeable to microorganisms so that the dressing remains sterile.

The dressing layer (12) is a hydrocolloid dressing of known type. It consists of absorbent particles (22) of sodium carboxymethylcellulose alone or with starch or other moisture absorbing particles, suspended in a layer (24) of polyisobutylene, which may be mixed with one or more other polymers, for example polyethylene. The degree of moisture retention of the dressing layer can be manipulated by changing the proportions of sodium carboxymethylcellulose, starch and any other moisture absorbing particles present. Polyisobutylene is a mobile polymer, which retains moisture so that the wound does not dry out, and which does not cause an adverse reaction to a patient. The permeability of the dressing is proportional to its thickness and may also be affected if the dressing is sterilized by irradiation. Because polyisobutylene is impermeable to moisture, the dressing layer is impermeable until it becomes saturated. However, the weight ratio of carboxymethylcellulose to polyisobutylene is chosen such that, when the dressing is saturated, it is possible for moisture to pass through the dressing layer and reach the indicator layer (14). A suitable ratio would be 1:1.

The indicator layer (14) is powdered gentian violet spread on the outer surface of the dressing layer (12). The gentian violet powder is held in place by the indicator bonding layer (16), which is formed from polyisobutylene or another mobile sticky polymer. Polyisobutylene is water impermeable and so the bonding layer prevents moisture from reaching the outside of the dressing. The bonding layer (16) has a thickness of about 0.5 mm so that it is transparent or translucent.

The outer covering (18) is formed from a flexible thin polyethylene film with holes about every 0.25 mm. A suitable film is marketed by Tredgar Films under the trade mark FLEXIFILM. The polyethylene film has negligible elasticity but the perforations in the film allow it to conform to any shape without folding or creasing.

In operation, the release paper (10) is removed from the dressing and the dressing is placed over a wound. The dressing is suitable for any wound of the type for which an occlusion dressing is generally used. The mobile polymer used in the hydrocolloid dressing layer (12) and in the indicator bonding layer (16) and, in particular the flexible polyethylene outer covering (18) ensure that the dressing will conform to the shape of the patient's body in the area of the wound. This is particularly useful as it avoids traumatic stress, which frequently causes irritation in the area surrounding the wound and may retard the healing process. In addition, the flexibility of the dressing means that the patient retains some mobility in the area of the wound. Thus, the dressing can be used even on an area such as a knee or elbow without the usual problems of creasing of the dressing, pressure on the wound and discomfort to the patient.

The hydrocolloid dressing layer (12) is water impermeable until the dressing becomes saturated and this ensures that the wound remains moist so that the healing process can progress. When the dressing becomes saturated, however, and requires changing, the hydrocolloid dressing layer (12) becomes permeable to water. Water passes through the dressing layer (12) and reaches the indicator layer (14) turning the gentian violet dye to a purple colour. This purple colour is visible through the transparent or translucent indicator bonding layer (16) and outer covering (18) and advises the person responsible for attending to the wound that the dressing is saturated and requires changing.

The moisture from the wound does not reach the outer surface of the dressing because the indicator bonding layer (16) is not permeable to water. This means that the patient's clothes or bedclothes do not become soiled. In addition, the water impermeable indicator bonding layer (16) means that any dirt on the outer surface of the dressing will not reach the wound and, further, that the dressing is easy to clean if the outer surface does become soiled.

Thus, the dressing of the present invention has the advantages of being easy to apply to a wound with little discomfort to a patient and of indicating to a carer when it needs to be changed.

What is claimed is:

1. A wound dressing comprising:
   a. a covering release layer;
   b. a dressing layer; and,
   c. an outer covering formed from a porous breathable film of low density polyethylene having a thickness of from 1 to 20 μm and perforations spaced at intervals of from 0.1 to 0.5 mm.

2. A wound dressing as claimed in claim 1, wherein the covering release layer comprises a paper with a siliconised surface and the dressing layer is of the hydrocolloid type.

3. A wound dressing as claimed in claim 1, wherein the covering release layer comprises a paper with a polymer coated surface and the dressing layer is of the hydrocolloid type.

4. An indicator wound dressing comprising:
   (a) a transparent or translucent outer covering;
   (b) a moisture-absorbing dressing layer which retains absorbed moisture in the area of a wound over which it is placed, the dressing layer remaining impermeable to moisture until it becomes saturated and comprising a gelling substance comprising sodium carboxymethylcellulose, alone or with starch or other moisture absorbing particles in a suspending agent comprising polyisobutylene, optionally mixed with polyethylene or other polymers, the ratio of gelling substance to suspending agent being about 1:1; and,
   (c) an indicator layer positioned between the outer covering and the dressing layer, the indicator layer changing color on contact with moisture thereby indicating when the dressing layer has become saturated and hence water-permeable.

5. An indicator wound dressing comprising:
   (a) a transparent or translucent outer covering;
   (b) a moisture-absorbing dressing layer which retains absorbed moisture in the area of a wound over which it is placed, the dressing layer remaining impermeable to moisture until it becomes saturated; and,
   (c) an indicator layer positioned between the outer covering and the dressing layer, the indicator layer comprising a soluble dye and including about 0.25% crystal green, cobalt salt moisture indicator or gentian violet.

6. A indicator wound dressing comprising:
   (a) a transparent or translucent outer covering composed of two sub-layers, an indicator bonding layer and an outer covering layer, the indicator bonding layer being from about 0.1 mm to 1.0 mm in thickness;
   (b) a moisture-absorbing dressing layer which retains absorbed moisture in the area of a wound over which it is placed, the dressing layer remaining impermeable to moisture until it becomes saturated; and, (c) an indicator layer positioned between the outer covering and the dressing layer, the indicator layer changing color on contact with moisture thereby indicating when the dressing layer has become saturated and hence water-permeable.

7. An indicator wound dressing comprising:

(a) a transparent or translucent outer covering composed of two sub-layers, an indicator bonding layer and an outer covering layer and the outer covering being formed from a porous breathable film of low density polyethylene having a thickness of from 1 to 20 $\mu$m and perforations spaced at intervals of from 0.1 to 0.5 mm;

(b) a moisture-absorbing dressing layer which retains absorbed moisture in the area of a wound over which it is placed, the dressing layer remaining impermeable to moisture until it becomes saturated; and, (c) an indicator layer positioned between the outer covering and the dressing layer, the indicator layer changing color on contact with moisture, thereby indicating when the dressing layer has become saturated and hence water-permeable.

* * * * *

UNITED STATES PATENT AND TRADEMARK OFFICE
CERTIFICATE OF CORRECTION

PATENT NO.    : 6,559,351 B1
DATED         : May 6, 2003
INVENTOR(S)   : Thomas George Eakin It is certified that error appears in the above-identified patent and that said Letters Patent is hereby corrected as shown below:

Column 2,
Line 44, delete the word "carboxymethylcefiulose" and insert
-- carboxymethylcellulose -- therefor.
Line 64, delete the word "hydroxymethylceUulose" and insert
-- hydroxymethylcellulose -- therefor.

Column 3,
Line 14, delete the word "Mercurochromet™" and insert -- Mercurochrome™ -- therefor.

Signed and Sealed this

Eighteenth Day of November, 2003

JAMES E. ROGAN
*Director of the United States Patent and Trademark Office*